United States Patent
Malek et al.

(10) Patent No.: US 10,654,035 B2
(45) Date of Patent: May 19, 2020

(54) CATALYST REGENERATION

(71) Applicant: Dow Global Technologies LLC, Midland, MI (US)

(72) Inventors: Andrzej Malek, Midland, MI (US); David Gordon Barton, Midland, MI (US); Lin Luo, Freeport, TX (US)

(73) Assignee: Dow Global Technologies LLC, Midland, MI (US)

( * ) Notice: Subject to any disclaimer, the term of this patent is extended or adjusted under 35 U.S.C. 154(b) by 0 days.

(21) Appl. No.: 16/079,362

(22) PCT Filed: Feb. 22, 2017

(86) PCT No.: PCT/US2017/018902
§ 371 (c)(1),
(2) Date: Aug. 23, 2018

(87) PCT Pub. No.: WO2017/151361
PCT Pub. Date: Sep. 8, 2017

(65) Prior Publication Data
US 2019/0046968 A1    Feb. 14, 2019

Related U.S. Application Data

(60) Provisional application No. 62/301,856, filed on Mar. 1, 2016.

(51) Int. Cl.
*B01J 38/44* (2006.01)
*B01J 38/18* (2006.01)
(Continued)

(52) U.S. Cl.
CPC .............. *B01J 38/44* (2013.01); *B01J 21/12* (2013.01); *B01J 23/08* (2013.01); *B01J 23/62* (2013.01);
(Continued)

(58) Field of Classification Search
None
See application file for complete search history.

(56) References Cited

U.S. PATENT DOCUMENTS

| 1,499,297 A | 6/1924 | De Mattia |
| 3,986,982 A | 10/1976 | Crowson et al. |

(Continued)

FOREIGN PATENT DOCUMENTS

| GB | 1499297 | 1/1978 |
| WO | 03/086625 | 10/2003 |
| WO | 2014035590 | 6/2014 |

OTHER PUBLICATIONS

International Search Report & Written Opinion for related PCT Application PCT/US2017/018902, dated Jun. 2, 2017 (19 pgs).

(Continued)

*Primary Examiner* — Ali Z Fadhel
(74) *Attorney, Agent, or Firm* — Brooks, Cameron & Huebsch, PLLC

(57) ABSTRACT

The present disclosure provides an air-soak containing regeneration process reducing its time. The process includes (i) removing surface carbon species from a gallium-based alkane dehydrogenation catalyst in a combustion process in the presence of a fuel gas; (ii) conditioning the gallium-based alkane dehydrogenation catalyst after (i) in air-soak treatment at a temperature of 660° C. to 850° C. with (iii) a flow of oxygen-containing gas having (iv) 0.1 to 100 parts per million by volume (ppmv) of a chlorine source selected from chlorine, a chlorine compound or a combination thereof; and achieving a predetermined alkane conversion percentage for the gallium-based alkane dehydrogenation catalyst undergoing the air-soak containing regeneration process using (i) through (iv) 10% to 50% sooner in air-soak treatment than that required to achieve the same predetermined alkane conversion percentage for the gallium-based (Continued)

alkane dehydrogenation catalyst undergoing the air-soak containing regeneration process using (i) through (iii), but without (iv).

16 Claims, 1 Drawing Sheet

(51) Int. Cl.
| | |
|---|---|
| *B01J 23/62* | (2006.01) |
| *B01J 23/96* | (2006.01) |
| *B01J 38/30* | (2006.01) |
| *B01J 38/34* | (2006.01) |
| *B01J 23/08* | (2006.01) |
| *B01J 23/92* | (2006.01) |
| *C07C 5/32* | (2006.01) |
| *B01J 38/14* | (2006.01) |
| *B01J 35/10* | (2006.01) |
| *B01J 38/02* | (2006.01) |
| *B01J 35/02* | (2006.01) |
| *B01J 21/12* | (2006.01) |

(52) U.S. Cl.
CPC ............... *B01J 23/92* (2013.01); *B01J 23/96* (2013.01); *B01J 35/023* (2013.01); *B01J 35/1014* (2013.01); *B01J 38/02* (2013.01); *B01J 38/14* (2013.01); *B01J 38/18* (2013.01); *B01J 38/30* (2013.01); *B01J 38/34* (2013.01); *C07C 5/321* (2013.01); *C07C 5/325* (2013.01); *C07C 2523/58* (2013.01); *C07C 2523/62* (2013.01); *Y02P 20/52* (2015.11); *Y02P 20/584* (2015.11)

(56) References Cited

U.S. PATENT DOCUMENTS

| | | | |
|---|---|---|---|
| 4,480,046 A | 10/1984 | Fung et al. | |
| 4,738,939 A | 4/1988 | Boyle | |
| 4,872,970 A | 10/1989 | Boyle | |
| 5,227,566 A * | 7/1993 | Cottrell | B01J 23/96 |
| | | | 502/34 |
| 5,401,705 A | 3/1995 | Amelse | |
| 9,834,496 B2 | 12/2017 | Pretz et al. | |
| 2010/0236985 A1 | 9/2010 | Lou et al. | |
| 2012/0277089 A1* | 11/2012 | Iyer | B01J 29/44 |
| | | | 502/35 |
| 2014/0200385 A1* | 7/2014 | Pretz | B01J 23/62 |
| | | | 585/660 |

OTHER PUBLICATIONS

2nd Written Opinion for related PCT Application PCT/US2017/018902, dated Apr. 10, 2018 (11 pgs).
International Preliminary Report on Patentability for related PCT Application PCT/US2017/018902, dated Jun. 12, 2018 (21 pgs).
D'Aniello, et al., "The Redispersion of Sintered Pt, Rh, and Pt/Rh Catalysts";Journal of Catalysts, vol. 109, pp. 407-422 (16 pgs) (1988).
Foger, et al., "The Effect of Chlorine Treatment on the Dispersion of Platinum Metal Particles Supported on Silica and y-Alumina"; Journal of Catalysts, vol. 92, pp. 64-78 (15 pgs) (1985).
Argyle, et al., "Heterogeneous Catalyst Deactivation and Regeneration: A Review"; Journal of Catalysts, vol. 5, pp. 145-269 (125 pgs) (Feb. 26, 2015).

* cited by examiner

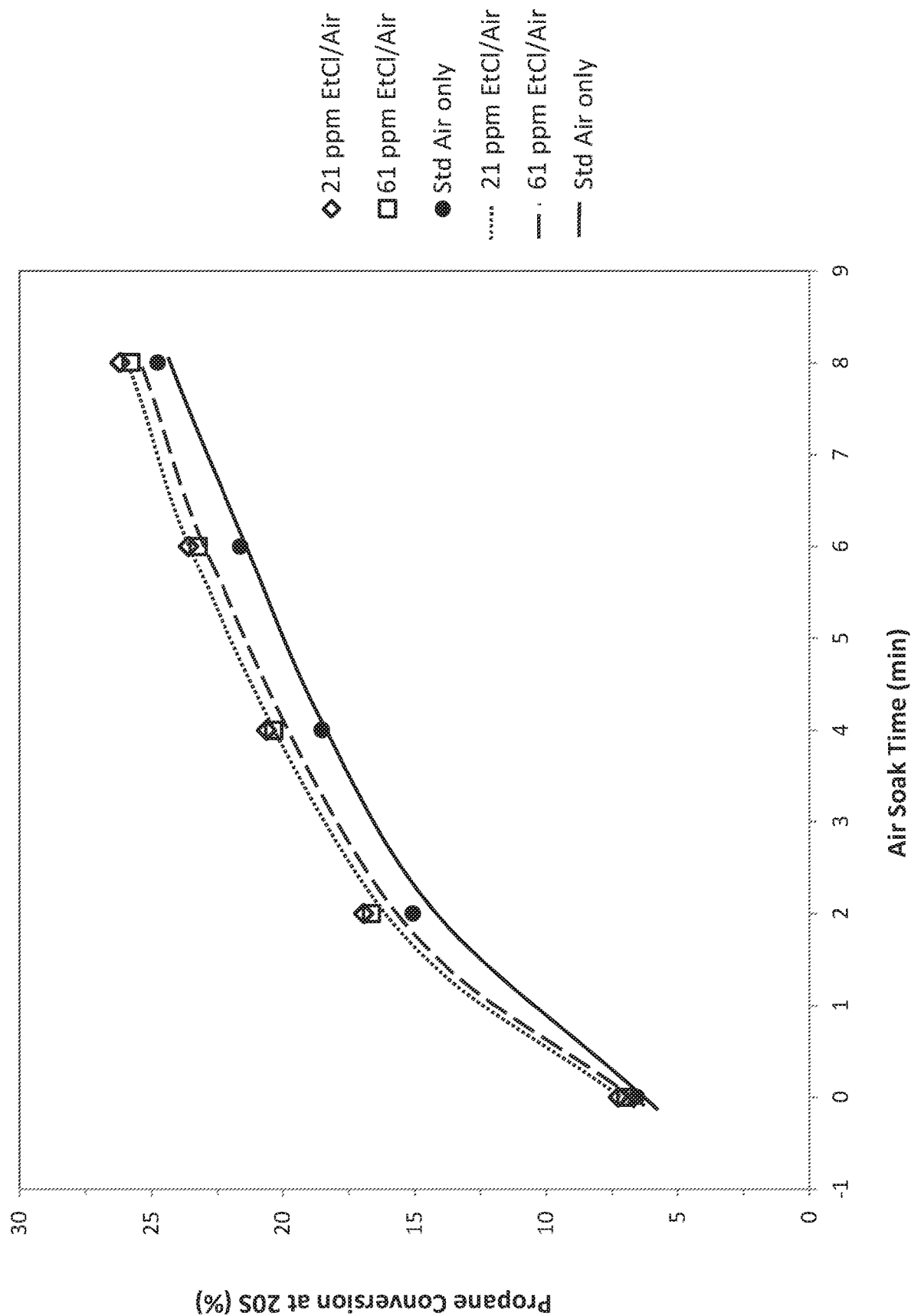

CATALYST REGENERATION

This application is a National Stage Application under 35 U.S.C. § 371 of International Application Number PCT/US2017/018902, filed Feb. 22, 2017 and published as WO 2017/151361 A1 on Sep. 8, 2017, which claims the benefit to U.S. Provisional Application 62/301,856, filed Mar. 1, 2016, the entire contents of which are incorporated herein by reference in its entirety.

TECHNICAL FIELD

The present disclosure relates generally to industrial processes, and more particularly to catalysis regeneration.

BACKGROUND

Conventional regeneration processes for catalysts with a reduced catalytic activity typically include removal of coke deposits from the catalyst surface. Treating catalysts to remove coke typically includes contacting such catalysts with air or another oxygen-containing gas at high temperatures (e.g. at least ≥450 degrees Celsius (° C.) for an ethanol dehydrogenation catalyst and ≥650° C. for a fluid catalyst cracking (FCC) catalyst)). Depending on the type of catalyst, additional treatment may be necessary, such as, re-dispersion and reduction (in the case of platinum-tin based dehydrogenation catalysts) and reduction alone in the case of palladium based acetylene removal catalysts. When applied to gallium-based alkane dehydrogenation catalysts, the conventional catalyst regeneration processes do not, however, fully restore or even substantially fully restore catalytic activity of gallium-based dehydrogenation catalysts to a level equaling or even approaching that of fresh, unused dehydrogenation catalysts. Those who practice alkane dehydrogenation, especially propane dehydrogenation (PDH), understand that as activity of a catalyst decreases, alkene production also decreases with a negative impact on the process economics.

For gallium-based catalysts, one approach to restoring the activity of alkane dehydrogenation catalysts is to include an air-soak step after the coke combustion step in the presence of additional fuel (Ref. WO 2013/009820). Deactivated gallium-based alkane dehydrogenation catalysts, however, require a prolonged air-soak treatment during its regeneration to restore and sustain activity cycle to cycle. Longer air-soak times translate to larger catalyst inventory and larger regenerator equipment impacting capital and operating cost of the alkane dehydrogenation process. Reducing the required air-soak time would help to improve the alkane dehydrogenation process performance and economics.

SUMMARY

The present disclosure has surprisingly discovered that adding a low concentration of a chlorine compound to an air-soak treatment in a regeneration process can reduce the time of the air-soak treatment required to achieve a predetermined alkane conversion percentage for a gallium-based alkane dehydrogenation catalyst as compared to achieving the same predetermined alkane conversion percentage for the gallium-based alkane dehydrogenation catalyst undergoing the air-soak treatment in a regeneration process without using the chlorine compound in the air-soak treatment. This discovery allows for the gallium-based alkane dehydrogenation catalyst undergoing the air-soak treatment in a regeneration process of the present disclosure to be brought back into service more quickly while achieving the required activity improvement cycle to cycle. As a result, less catalyst inventory and smaller regenerator equipment may be required thereby having a potential impact on capital and operating costs of the alkane dehydrogenation process.

To this end, the present disclosure provides for a method of reducing a time of an air-soak treatment in a regeneration process that includes (i) removing surface carbon species from a gallium-based alkane dehydrogenation catalyst in a combustion process using a fuel gas; (ii) conditioning the gallium-based alkane dehydrogenation catalyst after (i) in the air-soak treatment at a temperature of 660 degree Celsius (° C.) to 850° C. with (iii) a flow of oxygen-containing gas having (iv) 0.1 to 100 parts per million by volume (ppmv) of a chlorine source selected from chlorine, a chlorine compound or a combination thereof. This method results in achieving a predetermined alkane conversion percentage for the gallium-based alkane dehydrogenation catalyst undergoing the air-soak containing regeneration process using (i) through (iv) at least 10% to 50% sooner in the air-soak treatment than a time required for an air-soak treatment to achieve the same predetermined alkane conversion percentage for the gallium-based alkane dehydrogenation catalyst undergoing the air-soak treatment containing regeneration process using (i) through (iii), but without (iv).

For example, achieving the predetermined alkane conversion percentage of 10 percent under a weight hourly space velocity (WHSV) condition (100 hr$^{-1}$) and a reaction temperature of 620° C. for the gallium-based alkane dehydrogenation catalyst occurs 26 to 33 percent sooner in air-soak treatment for the gallium-based alkane dehydrogenation catalyst undergoing the air-soak containing regeneration process using (i) through (iv) as compared to the gallium-based alkane dehydrogenation catalyst undergoing the air-soak containing regeneration process using (i) through (iii), but without (iv).

In an additional example, achieving the predetermined alkane conversion percentage of 15 percent at a weight hourly space velocity of 100 hr$^{-1}$ and a reaction temperature of 620° C. for the gallium-based alkane dehydrogenation catalyst occurs 22 to 26 percent sooner in air-soak treatment for the gallium-based alkane dehydrogenation catalyst undergoing the air-soak containing regeneration process using (i) through (iv) as compared to the gallium-based alkane dehydrogenation catalyst undergoing the air-soak containing regeneration process using (i) through (iii), but without (iv).

Achieving the predetermined alkane conversion percentage of 20 percent at a weight hourly space velocity of 100 hr$^{-1}$ and a reaction temperature of 620° C. for the gallium-based alkane dehydrogenation catalyst occurs 27 to 31 percent sooner in air-soak treatment for the gallium-based alkane dehydrogenation catalyst undergoing the air-soak containing regeneration process using (i) through (iv) as compared to the gallium-based alkane dehydrogenation catalyst undergoing the air-soak containing regeneration process using (i) through (iii), but without (iv). Finally, achieving the predetermined alkane conversion percentage of 22 percent at a weight hourly space velocity of 100 hr$^{-1}$ and a reaction temperature of 620° C. for the gallium-based alkane dehydrogenation catalyst occurs 22 to 26 percent sooner in air-soak treatment for the gallium-based alkane dehydrogenation catalyst undergoing the air-soak containing regeneration process using (i) through (iv) as compared to the gallium-based alkane dehydrogenation catalyst undergoing the air-soak containing regeneration process using (i) through (iii), but without (iv).

As discussed herein, removing surface carbon species from the gallium-based alkane dehydrogenation catalyst occurs in a combustion process using fuel gas. As discussed herein, fuel gas includes a hydrocarbon based fuel, a hydrogen based fuel or a combination thereof. Using the fuel gas allows for sufficient heat to be generated to reheat the catalyst to a temperature required for the propane dehydrogenation. Using the fuel gas in the combustion step, however, negatively affects catalyst activity rendering the catalyst less active after this step (i) then beforehand. The air-soak treatment, as provided herein, is required to recover catalyst activity.

Conditioning the gallium-based alkane dehydrogenation catalyst after (i) in the air-soak treatment can include using (iii) with 5 to 90 ppm of the chlorine source. More specifically, conditioning the gallium-based alkane dehydrogenation catalyst after (i) in the air-soak treatment includes using (iii) with 21 to 61 ppm of the chlorine source. Conditioning the gallium-based alkane dehydrogenation catalyst after (i) in the air-soak treatment also includes conditioning the gallium-based alkane dehydrogenation catalyst at a temperature in a range from 680° C. to 770° C.

The gallium-based alkane dehydrogenation catalyst includes a platinum (Pt) based promoter and an optional promotor metal on a catalyst support selected from the group consisting of silica, alumina, silica-alumina composites, rare earth modified alumina, and combinations thereof. Preferably, the optional promotor metal is potassium (K). The Pt based promoter provides a Pt loading of 0.1 to 500 parts per million (ppmw) and the optional promoter has a K loading of 0 to 1 weight percent based on the total weight of the catalyst. Chlorine compound is selected from the group consisting of chlorinated hydrocarbons, HCl gas, chlorine ($Cl_2$) gas, and combinations thereof.

BRIEF DESCRIPTION OF THE DRAWINGS

FIG. 1 illustrates propane conversion after 30 reaction cycles with three different levels of monochloroethane used in the air-soak containing regeneration process for the gallium-based alkane dehydrogenation catalyst of the present disclosure.

DETAILED DESCRIPTION

As discussed herein, regeneration of a gallium-based dehydrogenation catalyst for the present disclosure involve at least the following steps. First, there is a combustion process that removes surface carbon species from the gallium-based alkane dehydrogenation catalyst. The combustion process uses a fuel gas in order to provide sufficient heat needed for the dehydrogenation reaction. In addition to removing the carbon species and reheating the catalyst, however, the combustion process has a negative impact on the activity of the catalyst. In order to regain the catalytic activity, the gallium-based alkane dehydrogenation catalyst after removal of the carbon species undergoes conditioning in an air-soak treatment. Conditioning the gallium-based alkane dehydrogenation catalyst in the air-soak treatment occurs at a temperature of 660 degree Celsius (° C.) to 850° C. with a flow of oxygen-containing gas. The flow of oxygen-containing gas is substantially free of the fuel gas or fuel combustion byproducts. The flow of oxygen-containing gas helps to strip at least a portion of the compounds from the combustion process from the gallium-based alkane dehydrogenation catalyst.

The present disclosure has surprisingly discovered, however, that using a chlorine compound at a predetermined concentration during the air-soak treatment can reduce the amount of time required for the air-soak treatment to achieve a predetermined alkane conversion percentage for a gallium-based alkane dehydrogenation catalyst undergoing the regeneration process. This reduction in time for the air-soak treatment is observed when compared to achieving the same predetermined alkane conversion percentage for the gallium-based alkane dehydrogenation catalyst undergoing the regeneration process without using the chlorine compound in an air-soak treatment. This discovery allows for the gallium-based alkane dehydrogenation catalyst undergoing the air-soak containing regeneration process of the present disclosure to be brought back into service more quickly while achieving and sustaining robust catalytic activity cycle to cycle. As a result, less catalyst inventory and smaller regenerator equipment may be required thereby having a potential impact on capital and operating costs of the alkane dehydrogenation process.

The present disclosure uses the chlorine compound at levels no greater than 0.01 percent by volume (i.e., no greater than 100 parts per million by volume) in an air-soak treatment in the regeneration process. Surprisingly, such low levels of the chlorine compound have a surprising effect on the time required for the air-soak treatment to achieve a predetermined alkane conversion percentage for a gallium-based alkane dehydrogenation catalyst undergoing the regeneration process. As discussed herein, these low concentrations of chlorine compounds are used with relatively high air-soak treatment temperatures during the regeneration process for the gallium-based alkane dehydrogenation catalyst. As discussed herein, the present disclosure provides for, among other things, a method of reducing a time of an air-soak treatment in a regeneration process that includes at least the following steps (i) through (iv):

(i) removing surface carbon species from a gallium-based alkane dehydrogenation catalyst in a combustion process using a fuel gas;

(ii) conditioning the gallium-based alkane dehydrogenation catalyst after (i) in the air-soak treatment at a temperature of 660 degree Celsius (° C.) to 850° C. with (iii) a flow of oxygen-containing gas having (iv) 0.1 to 100 parts per million by volume (ppmv) of a chlorine source selected from chlorine, a chlorine compound or a combination thereof.

In the first step (i), surface carbon species are removed from the gallium-based alkane dehydrogenation catalyst in a combustion process in the presence of a fuel gas to provide a gallium-based alkane dehydrogenation catalyst that is substantially free of surface carbon species. As used herein, "substantially free" refers to an amount of a compound, a moiety and/or an element in an identified material that is less than 0.05 percent by weight (wt %), based upon a given total weight. So, for example, as used herein, "substantially free of surface carbon species" refers to a catalyst that has a surface carbon species content of less than 0.05 percent by weight (wt %), based upon total catalyst weight. As used herein, "fuel gas" is a hydrocarbon or a hydrocarbon and a hydrogen based fuel for the combustion process. The hydrocarbon for the fuel gas can include C1 to C6 hydrocarbons or mixtures thereof. An oxygen source for the combustion process can be supplied through standard air or other source of oxygen as are known.

As provided herein, surface carbon species can include solid carbonaceous materials that can act to deactivate the alkane dehydrogenation catalyst. Coke formation is one of the most prominent types of catalytic deactivation. For the present disclosure, surface carbon species can form on the gallium-based alkane dehydrogenation catalyst during its use in alkane dehydrogenation. During this process, an alkane is brought into operative contact with the gallium-based alkane dehydrogenation catalyst in a reactor. During the course of its use, the gallium-based alkane dehydrogenation catalyst becomes deactivated, where after the loss of a predetermined amount of activity the catalyst becomes a partially deactivated catalyst, which needs regeneration. A "partially deactivated" catalyst means a catalyst with a dehydrogenation activity that is at least 70%, but less than 95%, of the dehydrogenation activity of the same catalyst prior to its use in dehydrogenation, (otherwise known as "regenerated" catalyst). The partially deactivated dehydrogenation catalyst can have a coke level of, for example, less than 0.3 percent by weight (wt. %) based upon total partially deactivated catalyst weight. After the first step (i), as discussed herein, the dehydrogenation catalyst is fully deactivated. A fully deactivated catalyst refers to a catalyst with a dehydrogenation activity that is less than 70% of the dehydrogenation activity of the same catalyst prior to its use in dehydrogenation, (otherwise known as "regenerated" catalyst).

The gallium-based alkane dehydrogenation catalyst can initially undergo a process step to remove the surface carbon species (e.g., coke and other carbonaceous materials). Removing surface carbon species includes exposing the surface carbon species from the gallium-based alkane dehydrogenation catalyst to a combustion process in which the fuel gas is added and combusted for a predetermined time. During this process, the gallium-based alkane dehydrogenation catalyst can be heated to a temperature of at least 660 degrees Celsius (° C.) using heat generated by combusting the fuel gas.

The gallium-based alkane dehydrogenation catalyst is then subjected to the (ii) conditioning step, according to the present disclosure. The step (ii) of conditioning the gallium-based alkane dehydrogenation catalyst after (i) removing surface carbon species occurs in the air-soak treatment step. The air-soak treatment occurs at a temperature of 660° C. to 850° C., where the gallium-based alkane dehydrogenation catalyst is exposed to (iii) the flow of oxygen-containing gas having 0.1 to 100 parts per million by volume (ppmv) of the chlorine source. Preferably, conditioning the gallium-based alkane dehydrogenation catalyst after (i) in the air-soak treatment includes conditioning the gallium-based alkane dehydrogenation catalyst can occur at a temperature in a range from 680° C. to 770° C.

As used herein, oxygen-containing gas preferably has an oxygen content within a range of from 5 mol % to 100 mol %, each mol % being based upon total moles of oxygen in the oxygen-containing gas. The oxygen-containing gas is preferably selected from a group consisting of standard air and molecular oxygen ($O_2$). The oxygen-containing gas may include an amount of nitrogen ($N_2$) such as that normally contained in air. The oxygen-containing gas is preferably substantially free of combustible hydrocarbons, carbon oxides (especially carbon monoxide and carbon dioxide) and water vapor.

The chlorine source can be selected from chlorine ($Cl_2$), a chlorine compound or a combination thereof. The chlorine compound is selected from the group consisting of chlorinated hydrocarbons, HCl gas and combinations thereof. Chlorinated hydrocarbons can be selected from the group consisting of monochloroethane, ethylene dichloride, carbon tetrachloride, propylchloride, butylchloride, and chloroform.

The gallium-based alkane dehydrogenation catalyst of the present disclosure preferably comprises gallium (Ga), a noble metal based promoter selected from the group consisting of platinum (Pt), palladium (Pd), rhodium (Rh) and iridium (Ir), and, an optional promoter metal (e.g. an alkali metal). The noble metal is preferably a platinum based promoter and the optional promoter metal is preferably potassium (K). The noble metal based promoter provides a noble metal (e.g., Pt) loading of 0.1 to 500 parts per million (ppm) based on the total weight of the catalyst. The optional promoter can have a K loading of 0 to 1 weight percent based on the total weight of the catalyst.

The gallium-based alkane dehydrogenation catalyst can include a support, as are known. Examples of such supports include, but are not limited to, aluminium oxide ($Al_2O_3$), silicon dioxide, silica-alumina composites, rare earth modified alumina, and combinations thereof. Preferably, the support is aluminium oxide.

The gallium-based alkane dehydrogenation catalyst provided herein is particularly well suited for the dehydrogenation of propane. While particularly suitable for dehydrogenating propane, the improved process also has utility in dehydrogenating other alkanes, including ethane, butane, and pentane to their respective alkenes (e.g. ethylene when the alkane is ethane). The alkene (e.g. propylene, ethylene or butylene) has utility as a monomer in polymerization processes to produce, for example, polyethylene, polypropylene or an ethylene-propylene copolymer.

During step (ii) of conditioning, the gallium-based alkane dehydrogenation catalyst is exposed to the flow of oxygen-containing gas having 0.1 to 100 ppmv of the chlorine source during the air-soak treatment. Preferably, (ii) conditioning the gallium-based alkane dehydrogenation catalyst after (i) in the air-soak treatment can include using (iii) a flow of oxygen-containing gas having (iv) 5 to 90 ppm of the chlorine source. More preferably, (ii) conditioning the gallium-based alkane dehydrogenation catalyst after (i) in the air-soak treatment includes using (iii) a flow of oxygen-containing gas having (iv) 21 to 61 ppm of the chlorine source.

The gallium-based alkane dehydrogenation catalyst is exposed to the flow of oxygen-containing gas having the chlorine source during the air-soak treatment for a time in a range from 0.5 minutes to 14 minutes. Preferably, the air-soak treatment can be from at least two (2) minutes to 14 minutes, preferably at least three (3) minutes to 14 minutes, and more preferably from three (3) minutes to 14 minutes. The time the gallium-based alkane dehydrogenation catalyst is exposed to the flow of oxygen-containing gas having the chlorine source can also be in a range from 0.5 minutes to 8 minutes or from 1.5 minutes to 8 minutes.

Steps (i) and (ii) through (iv) may occur in an apparatus or combination of apparatuses suitable for effecting actions specified in each of such steps. In some embodiments, step (i) is physically separated from steps (ii) through (iv). In such embodiments, physical separation may occur by using a first apparatus or vessel for step (i) and a second apparatus or vessel for steps (ii) through (iv). Instead of using separate apparatuses, one may interpose physical barriers (e.g. baffles) within a single apparatus to control, minimize or, preferably, eliminate uncontrolled movement of at least one of gases and catalyst in a reverse direction (e.g. from step ii) back to step (i), a phenomenon sometimes referred to as "backflow" or "back-mixing." Alternately, one may use two apparatuses or vessels, one with a physical barrier and one without a physical barrier. Physical separation also allows one to use a first pressure (e.g. oxygen partial pressure) on one side of the physical separation, whether the separation is effected by a barrier within a single apparatus or by use of two separate apparatuses, and a second pressure, either higher or lower, on the other side of the physical separation.

Steps (i) and (ii) through (iv), whether physically separated from one another or not, preferably occur in a fluidized bed apparatus that operates in a bubbling, turbulent flow or fast fluid bed mode with a gas superficial velocity sufficient to effect rapid heat and mass transfer. If physically separated, one may independently select the pressure, temperature, apparatus or operating mode for each of steps (i) and (ii) through (iv). The gas superficial velocity is desirably higher than the minimum velocity needed to effect fluidization of the particles ($V_{mf}$) within the apparatus, preferably at least five times $V_{mf}$, more preferably at least 10 times $V_{mf}$ and still more preferably from 20 times $V_{mf}$ to 100 times $V_{mf}$. In order to minimize solid back mixing between steps (i) and (ii) through (iv), one may use internal mechanical devices within a fluid bed apparatus such as grids, trays, shed rows, or structured packing. The internal mechanical devices appear to promote contact between flowing gas and catalyst particles while minimizing possible formation of fuel gas or air bubbles of sufficient size to do one or more of creating hot spots, reducing fuel gas conversion or fuel gas combustion efficiency.

Using steps (i) through (iv) of the air-soak containing regeneration process of the present disclosure allows the gallium-based alkane dehydrogenation catalyst to achieve a predetermined alkane conversion percentage of at least 10 percent (%) to 50% sooner in air-soak treatment than that required to achieve the same predetermined alkane conversion percentage for the gallium-based alkane dehydrogenation catalyst undergoing the air-soak containing regeneration process using steps (i) through (iii), but without step (iv) provided herein. This reduction in the air-soak time required for the air-soak containing regeneration process to regenerate the gallium-based alkane dehydrogenation catalyst in turn allows for less catalyst inventory to be maintained, less energy costs for regenerating the gallium-based alkane dehydrogenation catalyst and for smaller scale regenerator equipment to be used in process. This results in a savings of both time and money.

As illustrated in the Examples section herein, when propane is used as the alkane in the alkane dehydrogenation process it was surprisingly observed that using relatively less of the chlorine source resulted in an equally or more rapid regeneration of the gallium-based alkane dehydrogenation catalyst. For example, when the steps (i) through (iv) where used to achieve a predetermined alkane conversion percentage of 10 percent under a weight hourly space velocity of 100 hr$^{-1}$ and reaction temp of 620° C. for the gallium-based alkane dehydrogenation catalyst it occurred 26 to 33 percent sooner in air-soak treatment as compared to the gallium-based alkane dehydrogenation catalyst undergoing the air-soak containing regeneration process using (i) through (iii), but without (iv). Surprisingly, however, for the same air-soak treatment temperature (730° C.) and chlorine source (monochloroethane), the 33 percent reduction in the air-soak treatment time to achieve the predetermined alkane conversion percentage of 10 percent occurred using a flow of oxygen-containing gas having 21 ppmv of the chlorine source, whereas the 26 percent reduction in the air-soak treatment time to achieve the predetermined alkane conversion percentage of 10 percent was achieved using the flow of oxygen-containing gas having 61 ppmv of the chlorine source.

In an additional example, when the steps (i) through (iv) where used to achieve a predetermined alkane conversion percentage of 15 percent under a high weight hourly space velocity of 100 hr$^{-1}$ and reaction temp of 620° C. for the gallium-based alkane dehydrogenation catalyst it occurred 22 to 26 percent sooner in air-soak treatment as compared to the gallium-based alkane dehydrogenation catalyst undergoing the air-soak containing regeneration process using (i) through (iii), but without (iv). Again, however, for the same air-soak treatment temperature (730° C.) and chlorine source (monochloroethane), the 26 percent reduction in the air-soak treatment time to achieve the predetermined alkane conversion percentage of 15 percent occurred using a flow of oxygen-containing gas having 21 ppmv of the chlorine source, whereas the 22 percent reduction in air-soak treatment time to achieve the predetermined alkane conversion percentage of 15 percent was achieved using the flow of oxygen-containing gas having 61 ppmv of the chlorine source.

In another example, when the steps (i) through (iv) where used to achieve a predetermined alkane conversion percentage of 20 percent under a high weight hourly space velocity of 100 hr$^{-1}$ and reaction temp of 620° C. for the gallium-based alkane dehydrogenation catalyst it occurred 27 to 31 percent sooner in air-soak treatment as compared to the gallium-based alkane dehydrogenation catalyst undergoing the air-soak containing regeneration process using (i) through (iii), but without (iv). Again, however, for the same air-soak treatment temperature (730° C.) and chlorine source (monochloroethane), the 31 percent reduction in the air-soak treatment time to achieve the predetermined alkane conversion percentage of 20 percent occurred using a flow of oxygen-containing gas having 21 ppmv of the chlorine source, whereas the 27 percent reduction in air-soak treatment time to achieve the predetermined alkane conversion percentage of 20 percent was achieved using the flow of oxygen-containing gas having 61 ppmv of the chlorine source.

In yet another example, when the steps (i) through (iv) where used to achieve a predetermined alkane conversion percentage of 22 percent under a high weight hourly space velocity of 100 hr$^{-1}$ and reaction temp of 620° C. for the gallium-based alkane dehydrogenation catalyst it occurred 22 to 26 percent sooner in air-soak treatment as compared to the gallium-based alkane dehydrogenation catalyst undergoing the air-soak containing regeneration process using (i) through (iii), but without (iv). Again, however, for the same air-soak treatment temperature (730° C.) and chlorine source (monochloroethane), the 26 percent reduction in air-soak treatment time to achieve the predetermined alkane conversion percentage of 22 percent occurred using a flow of oxygen-containing gas having 21 ppmv of the chlorine source, whereas the 22 percent reduction in air-soak treatment time to achieve the predetermined alkane conversion percentage of 22 percent was achieved using the flow of oxygen-containing gas having 61 ppmv of the chlorine source. Furthermore, the effect of the chlorine source in the air-soak is to some degree persistent, that is the shorter cycle improvement remains when chlorine addition is discontinued indicating that at least transient modification of the catalyst composition to include chlorine form the combustion of chlorine containing precursor is possible. Both continuous and intermittent feed of chlorine source compound could be used to realize the reduction of air-soak time.

The regenerated gallium-based alkane dehydrogenation catalyst can also undergo a stripping step to remove at least a portion of molecular oxygen and chlorine compound either trapped within or between catalyst particles and/or adsorbed to the surface of the gallium-based alkane dehydrogenation catalyst. The stripping step can occur at a temperature of at least 660° C. while exposing the air-soak treated catalyst to a flow of stripping gas that is substantially free of molecular oxygen, chlorine source and combustible fuel for a period of time sufficient to remove at least a portion of molecular oxygen and chlorine compound thereby producing a gallium-based alkane dehydrogenation catalyst that is ready for use in the reactor for alkane dehydrogenation. A practical upper limit for the stripping step is 850° C. to avoid challenges such as unwanted side reactions or damage to catalyst or apparatus components used in conjunction with the process. The temperature more preferably lies within a range of from 660° C. to 780° C., more preferably from 700° C. to 750° C. This stripping step preferably occurs in a fixed, packed, fluidized or moving bed with a flow of oxygen-free gas that is sufficient to effect removal of at least a portion of molecular oxygen trapped within or between catalyst particles and physisorbed oxygen that is desorbable from the catalyst particles.

The stripping step also preferably comprises maintaining the heated catalyst at a temperature within the temperature range and exposing the heated catalyst to a flow of oxygen-free gas, preferably an inert gas such as $N_2$, sufficient to remove at least a portion of, more preferably substantially all of residual combustion byproducts and residual oxygen present on the heated catalyst prior to exposure to the flow of oxygen-free gas. "Substantially all" means, in this context, that a heated catalyst subsequent to treatment with the oxygen-free gas preferably has carbon dioxide content of less than 1 wt % and a water content of less than 0.2 wt %, each wt % being based upon total heated catalyst weight.

The oxygen-free gas used in the stripping step may include small amounts of a carbon oxides, water vapor or both (e.g. no more than two (2) molar percent (mol %) water, no more than 1 mol % carbon dioxide and less than 0.1 mol % carbon monoxide, each mol % being based on total moles of oxygen-free gas), but the oxygen-free gas is preferably substantially free (less than 0.5 mol % water, less than 0.5 mol % carbon dioxide, each mol % being based on total moles of oxygen-free gas, and less than 200 parts by mole per million parts total moles of oxygen-free gas) of carbon oxides and water vapor.

As discussed herein, the steps for the regeneration of the gallium-based dehydrogenation catalyst for the present disclosure involves coke and fuel combustion, further air-soak treatment in oxygen containing gas stream substantially free of fuel and combustion products (air-soak treatment) and stripping of at least a portion of molecular oxygen and chlorine compound either trapped within or between catalyst particles and/or adsorbed to the surface of the dehydrogenation catalyst. Each of these steps can operate in the same fluidization regimes as the other steps or in different gas-solid fluidization regimes or even in a combination of fluidization regimes within each step. These regimes range from minimum fluidization to bubbling fluidization to turbulent bubbling fluidization to circulating fast-fluidization to dilute-phase gas-solid transport regime and incorporating technology known to those in the art to improve fluidization behavior within that fluidization regime, including grids, structured packing, or other internals.

For example, the combustion step may occur in a gas-solid counter-flow regenerator operating in the bubbling regime in which solid particles enter from the top of the process and flow downward, exiting at the bottom of a combustion zone while the combusting gas flows upward. The combustion step may, for example, also occur with gas-solid co-current flow (i.e. gas and solids flow in a single direction, either upward or downward in a vertical apparatus or vessel). Separately, the air-soak treatment step may, for example, occur in the same vessel below the combustion step and with the catalyst entering from the top of the vessel for the combustion step (exiting from the bottom of the vessel for the air-soak treatment step) and flowing downward, counter-currently to the oxidizing gas flowing upward and maintaining operation in a bubbling regime. Separately, the air-soak treatment step may occur in a separate zone or vessel and operating in a fluidization regime independent of the fluidization regime in the combustion step, including any fluidization regime from minimum gas-solid fluidization to gas-solid bubbling fluidization to turbulent bubbling fluidization to circulating fast-fluidization to dilute phase gas-solid transport regime. Similarly, the stripping step can occur either as a continuation of the fluidization regime of the air-soak treatment step or operate independently of the fluidization regime in the air-soak treatment step.

In some embodiments, physical separation of the combustion, air-soak treatment and stripping steps may be effected by use of a device such as an annular stripper. This provides a related benefit in allowing for an increased length to diameter (L to D) ratio within a device, apparatus or vessel used for the regeneration step relative to what one might use in the absence of physical separation (where D is defined as the actual diameter for traditional cylindrical cases and as the annular width for the annular cases). By way of example, conventional fluid catalyst cracking (FCC) bubbling bed regenerators are believed to have L to D ratios that range from 0.1:1 to 1.0:1 for coke combustion. L to D ratios for apparatus used in the stripping step preferably range from greater than 1.0:1 to 10:1 and more preferably from 2.0:1 to 6.0:1 for those embodiments of the present invention that physically separate the combustion and the air-soak treatment steps from the stripping step. In some embodiments, the apparatus used for the air-soak treatment step operates with a superficial gas velocity where the air-soak treatment commences (nominally the "bottom" of the regeneration zone) that ranges between 0.05 feet per second (ft/sec) (0.015 meter per second (m/sec)) to 0.5 ft/sec (0.15 m/sec), more preferably from 0.15 ft/sec (0.046 m/sec) to 0.4 ft/sec (0.0122 m/sec), and still more preferably from 0.2 ft/sec (0.061 m/sec) to 0.3 ft/sec (0.091 m/sec). Catalyst bed density within apparatus used for the air-soak treatment step desirably ranges from 45 pounds per cubic foot ($lb/ft^3$) (720.1 kilograms per cubic meter ($kg/m^3$)) to 70 $lb/ft^3$ (1121.3 $kg/m^3$), preferably from 50 $lb/ft^3$ (800.9 $kg/m^3$) to 65 $lb/ft^3$ (1041.2 $kg/m^3$), and more preferably from 55 $lb/ft^3$ (881.0 $kg/m^3$) to 60 $lb/ft^3$ (961.1 $kg/m^3$). In some embodiments, the apparatus used for the air-soak treatment operates with a pressure at that end of the apparatus remote from the nominal bottom, nominally the "top" or "top end" of such apparatus, ranging from 10 pounds per square inch absolute (psia) (68.9 kilopascals (kPa)) to 60 psia (413.7 kPa)), preferably from 25 psia (172.4 kPa) to 40 psia (275.8 kPa).

In some embodiments, at least a portion of catalyst may be recycled from the apparatus or apparatus portion used for the air-soak treatment step to the apparatus or apparatus portion used for the combustion step. Recycling from the nominal bottom of the apparatus used for the regeneration step may facilitate unit start-up for at least some embodiments of the improved process disclosed herein. Recycling from a nominal top of the apparatus used for the air-soak treatment step (i.e. an end remote from the nominal bottom end) to the apparatus or apparatus portion used for the combustion step can provide at least some of the catalyst needed for fuel combustion in the combustion step. In some embodiments, the air-soak treatment and stripping steps are physically separated in order to affect the air-soak treatment step at a higher oxygen partial pressure.

An inert gas preferably provides motive force to transport regenerated catalyst from the regenerator to the reactor. An inert gas is preferred over an oxygen containing gas because the latter will react with a reactant gas (an alkane such as propane) to form undesired byproducts such as carbon monoxide, carbon dioxide and possibly an oxygenate (the presence of such byproducts can adversely affects process economics). While small amounts of combustion byproducts, such as less than 0.1 mol. % of carbon monoxide, less than 1 mol. % of carbon dioxide and less than 0.5 mol. % of water may be present in an inert gas stream that provides motive force, each mol. % being based upon total moles of such inert gas stream, may be tolerated, increasing such amounts leads to a decrease in catalyst performance with small increases leading to small decreases in catalyst performance and larger increases leading to further decreases in catalyst performance. When oxygenates are present, one may also need an additional separation apparatus or facility to recover a desired alkene from a mixture of the alkene and an oxygenate. An inert gas is also preferred over a fuel gas such as hydrogen or methane because fuel gases lead to lower catalyst performance than one obtains with an inert gas.

The present disclosure is also believed to be applicable and beneficial in other techniques and methods of regenerating propane dehydrogenation catalysts. For example, PCT Patent Publication Number WO 2013/009820 entitled "Reactivating Propane Dehydrogenation Catalyst" to Pretz et al. provides for increasing propane dehydrogenation activity of a partially deactivated dehydrogenation catalyst by heating the partially deactivated catalyst to a temperature of at least 660° C. and conditioning the heated catalyst in an oxygen-containing atmosphere and, optionally, stripping molecular oxygen from the conditioned catalyst. PCT Patent Publication Number WO 2013/009820 is incorporated herein in its entirety.

According to WO 2013/009820, this improved process for dehydrogenating an alkane includes placing an alkane in operative contact with a heated alkane dehydrogenation catalyst in a reactor, the catalyst comprising a Group VIII noble metal, a Group IIIA metal and, optionally, a promoter metal, removing from the reactor a partially deactivated catalyst, rejuvenating the partially deactivated catalyst in a regenerator, and transporting the rejuvenated catalyst from the regenerator to the reactor, wherein the improvement comprises a combination of treatment within the regenerator and transport of the rejuvenated catalyst from the regenerator to the reactor, the treatment within the regenerator comprising sequential steps:

a. heating the partially deactivated catalyst to a temperature of at least 660 degrees Celsius using heat generated by combusting both coke contained on the partially deactivated catalyst and a fuel source other than the coke, the heating yielding a heated, further deactivated catalyst which has an alkane (e.g. propane) dehydrogenation activity that is less than that of the partially deactivated catalyst;

b. subjecting the heated, further deactivated catalyst to a conditioning step which comprises maintaining the heated, further deactivated dehydrogenation catalyst at a temperature of at least 660 degrees Celsius while exposing the heated, further deactivated dehydrogenation catalyst to a flow of an oxygen-containing gas for a period of time greater than two minutes and sufficient to yield an oxygen-containing reactivated dehydrogenation catalyst that has an activity for dehydrogenating alkane (e.g. propane) that is greater than that of either the partially deactivated catalyst or the further deactivated catalyst; and optionally, but preferably c. maintaining the oxygen-containing reactivated catalyst at a temperature of at least 660 degrees Celsius while exposing the reactivated catalyst to a flow of stripping gas that is substantially free of molecular oxygen and combustible fuel for a period of time sufficient to remove from the oxygen-containing reactivated dehydrogenation catalyst at least a portion of molecular oxygen trapped within or between catalyst particles and physisorbed oxygen that is desorbable at the temperature during that period of time and yield a rejuvenated dehydrogenation catalyst; with transport from the regenerator to the reactor being effected by a combination of gravity and motive force imparted by an inert transport gas. The rejuvenated dehydrogenation catalyst preferably has substantially the same activity for dehydrogenating propane as the reactivated dehydrogenation catalyst, but a lower activity for forming carbon oxides than the reactivated dehydrogenation catalyst.

As discussed herein, using the chlorine compound at a predetermined concentration in the air-soak containing regeneration process can reduce the amount of air-soak treatment time that is required to achieve a predetermined alkane conversion percentage for a gallium-based alkane dehydrogenation catalyst undergoing the air-soak containing regeneration process. As applied to WO 2013/009820, the present disclosure may allow for an improved process for dehydrogenating an alkane, the process comprising placing an alkane in operative contact with a heated alkane dehydrogenation catalyst in a reactor, the catalyst comprising a Group VIII noble metal, a Group IIIA metal and, optionally, a promoter metal, removing from the reactor a partially deactivated catalyst, rejuvenating the partially deactivated catalyst in a regenerator, and transporting the rejuvenated catalyst from the regenerator to the reactor, wherein the improvement comprises a combination of treatment within the regenerator and transport of the rejuvenated catalyst from the regenerator to the reactor, the treatment within the regenerator comprising sequential steps:

a. heating the partially deactivated catalyst to a temperature of at least 660 degrees Celsius using heat generated combustion products obtained by combusting both coke contained on the partially deactivated catalyst and a fuel source other than the coke, the heating yielding a heated, further deactivated catalyst which has an alkane dehydrogenation activity that is less than that of the partially deactivated catalyst;

b. subjecting the heated, further deactivated catalyst to a conditioning step which comprises maintaining the heated, further deactivated dehydrogenation catalyst at a temperature of at least 660 degrees Celsius while exposing the heated, further deactivated dehydrogenation catalyst to a flow of an oxygen-containing gas with a chlorine or chlorine containing compound with an overall Cl concentration 0.1 ppm-volume to 100 ppm-volume for a period of time sufficient to yield an oxygen-containing reactivated dehydrogenation catalyst that has an activity for dehydrogenating alkane that is greater than that of either the partially deactivated catalyst or the further deactivated catalyst; and, optionally, c. maintaining the oxygen-containing reactivated catalyst at a temperature of at least 660 degrees Celsius while exposing the reactivated catalyst to a flow of stripping gas that is substantially free of molecular oxygen and combustible fuel for a period of time greater than two minutes and sufficient to remove from the oxygen-containing reactivated dehydrogenation catalyst at least a portion of molecular oxygen trapped within or between catalyst particles and chemisorbed oxygen that is desorbable at the temperature during that period of time and yield a rejuvenated dehydrogenation catalyst; with transport from the regenerator to the reactor being effected by a combination of gravity and motive force imparted by an inert transport gas.

EXAMPLES

In the following paragraphs, Arabic numerals designate examples (Ex) of the disclosure and capital letters designate comparative examples (CEx).

Conduct experiments at ambient pressure (1 atmosphere (98.1 KPa)) under simulated circulating fluid bed operation conditions in a vertically-oriented, fixed bed quartz reactor.

For all Ex and CEx, use a supported gallium-platinum-potassium (Ga—Pt—K) catalyst. The catalyst has a metals content of 1.6 percent by weight (wt %) Ga, 0.25 wt % K and 200 parts per million by weight (ppmw) Pt, each wt % being based upon total catalyst weight and the ppm being based upon one million parts by weight of total catalyst weight. The support is a silica-modified alumina (SIRALOX™ 1.5/70, Sasol, 1.5 wt % $SiO_2$ in alumina, surface area of 70 square meters per gram ($m^2$/g), 80-100 micron particles).

Premix 65 mg of the catalyst at a 3:1 weight to weight (wt:wt) ratio of quartz chips:catalyst, the quartz chips having a height of 2 millimeter (mm) and a diameter of 2 mm (Quartz Scientific Inc.) and place the premix on the coarse frit in the center piece of the quartz reactor, where it is held in place by quartz wool. Insert the reactors into clamshell-type heaters (Micromeritics 291/53801/00).

To minimize the dead volume inside the reactor, quartz chips were loaded above the catalyst bed, however, below the catalyst, the quartz reactor funnels down to a capillary-sized opening. The thermocouple was placed on the outside of the reactor but touching the reactor wall and vertically positioned just below the catalyst plug.

Subject the 65 mg catalyst to multiple reaction/regeneration cycles as detailed below, each cycle comprised a reaction step and a regeneration step. Between reaction and regeneration steps, use an inert gas stripping step by adding nitrogen ($N_2$) gas at a flow rate of 60 standard cubic centimeter per minute (sccm). In the reaction step, test the propane dehydrogenation (PDH) activity at a reaction temperature of 620° C. with 100 mole percent propane ($C_3H_8$) feed at a flow rate of 60 sccm through the catalyst bed, which corresponded to weight hourly space velocity (WHSV) of 100 $hr^{-1}$ for a total time of 120 seconds.

Measure the product analysis for the propane conversion to $C_3H_6$ using an on-line Thermo Scientific process mass spectrometer (VG Prima Pro) at 5 second time intervals with the propane conversion reported after 20 seconds on stream. Specific details for each experiment are listed in Table 1. Following the reaction step, heat the catalysts to 730° C. in flowing nitrogen and then expose to the products of methane combustion with a composition of 16 weight percent (mol %) $H_2O$, 3 mol % $O_2$, 8 mol % $CO_2$, balance $N_2$ at 730° C. Immediately following exposure to combustion products, conduct the air-soak treatment step in flowing dry air at 730° C. with various amounts of monochloroethane (0 ppm—Cex A, 21 ppm—Ex 1, and 61 ppm—Ex 2) for the targeted air-soak times at a total flow rate of 60 sccm. Repeat reaction/combustion treatment/air-soak treatment cycles for 30 cycles at the targeted air-soak time. At the end of 30 cycles with the desired air-soak time, perform three cycles of reaction/combustion treatment/air-soak treatment with a long air-soak time (20 min) to reactivate the catalyst. Five targeted air-soak times were studied, 8, 6, 4, 2, and 0 min. The propane conversion results after 30 reaction/combustion treatment/air-soak treatment cycles are shown in FIG. 1.

|  | CEx A (0 ppm Mono-chloroethane) | Ex 1 (21 ppm Mono-chloroethane) | Ex 2 (61 ppm Mono-chloroethane) |
|---|---|---|---|
| Cycles | 30 | 30 | 30 |
|  |  | PDH reaction step |  |
| $T_{reaction}$ | 620° C | 620° C. | 620° C. |
| Reaction time | 2 min | 2 min | 2 min |
| $P_{reaction}$ | 7 psig | 8 psig | 7 psig |
|  |  | Combustion treatment step$^a$ |  |
| $T_{combustion\ gases}$ | 730° C. | 730° C. | 730° C. |
| Combustion time | 2 min | 2 min | 2 min |
| $P_{combustion\ gases}$ | 10 psig | 10 psig | 10 psig |
|  |  | Regeneration step$^a$ |  |
| $T_{regeneration}$ | 730° C. | 730° C. | 730° C. |
| Air-soak time | 8, 6, 4, 2, 0 min | 8, 6, 4, 2, 0 min | 8, 6, 4, 2, 0 min |
| $P_{regeneration}$ | 10 psig | 8 psig | 8 psig |

The results in FIG. 1 show that, after removing surface carbon species, the predetermined alkane conversion percentage for the gallium-based alkane dehydrogenation catalyst undergoing the air-soak containing regeneration process of the present disclosure is achieved 22 percent (%) to 33% sooner in air-soak treatment than that required to achieve the same predetermined alkane conversion percentage for the gallium-based alkane dehydrogenation catalyst undergoing the air-soak containing regeneration process, but not using the chlorine source as discussed herein.

Table 2 was generated from FIG. 1 with air-soak time extracted at constant conversion.

| Propane Conversion (%) | Air Soak Time Required | | | % Reduction in Soak Time | |
|---|---|---|---|---|---|
|  | Base Case | 61ppmEtCl/ Air | 21ppmEtCl/ Air | 61ppmEtCl/ Air | 21ppmEtCl/ Air |
| 10 | 0.7 | 0.5 | 0.4 | 26% | 33% |
| 15 | 2.1 | 1.6 | 1.5 | 22% | 26% |
| 20 | 4.9 | 3.5 | 3.4 | 27% | 31% |
| 22 | 6.5 | 5 | 4.8 | 22% | 26% |

What is claimed is:

1. A method of reducing a time of an air-soak treatment in a regeneration process, comprising:
   (i) removing surface carbon species from a gallium-based alkane dehydrogenation catalyst in a combustion process using a fuel gas; and
   (ii) conditioning, after the surface carbon species is removed from the gallium-based alkane dehydrogenation catalyst, the gallium-based alkane dehydrogenation catalyst in the air-soak treatment at a temperature of 660 degree Celsius (° C.) to 850° C. with (iii) a flow of oxygen-containing gas having (iv) 0.1 to 100 parts per million by volume (ppmv) of a chlorine source selected from chlorine, a chlorine compound or a combination thereof, wherein a predetermined alkane conversion percentage for the gallium-based alkane dehydrogenation catalyst undergoing the air-soak containing regeneration process is achieved using (i) through (iv) at least 10% to 50% sooner in air-soak treatment than a time required to achieve the same predetermined alkane conversion percentage for the gallium-based alkane dehydrogenation catalyst undergoing the air-soak treatment containing regeneration process using (i) through (iii), but without (iv).

2. The method of claim 1, wherein conditioning the gallium-based alkane dehydrogenation catalyst after (i) in the air-soak treatment includes using (iv) with 5 to 90 ppmv of the chlorine source.

3. The method of claim 2, wherein conditioning the gallium-based alkane dehydrogenation catalyst after (i) in the air-soak treatment includes using (iv) with 21 to 61 ppmv of the chlorine source.

4. The method of claim 2, wherein conditioning the gallium-based alkane dehydrogenation catalyst after (i) in air-soak treatment includes conditioning the gallium-based alkane dehydrogenation catalyst at a temperature in a range from 680° C. to 770° C.

5. The method of claim of claim 1, where achieving the predetermined alkane conversion percentage of 10% at a weight hourly space velocity of 100 h$^{-1}$ and a reaction temperature of 620° C. for the gallium-based alkane dehydrogenation catalyst occurs 26% to 33% sooner in air-soak treatment for the gallium-based alkane dehydrogenation catalyst undergoing the air-soak containing regeneration process using (i) through (iv) as compared to the gallium-based alkane dehydrogenation catalyst undergoing the air-soak containing regeneration process using (i) through (iii), but without (iv).

6. The method of claim 1, where achieving the predetermined alkane conversion percentage of 15% at a weight hourly space velocity of 100 h$^{-1}$ and a reaction temperature of 620° C. for the gallium-based alkane dehydrogenation catalyst occurs 22% to 26% sooner in air-soak treatment for the gallium-based alkane dehydrogenation catalyst undergoing the air-soak containing regeneration process using (i) through (iv) as compared to the gallium-based alkane dehydrogenation catalyst undergoing the air-soak containing regeneration process using (i) through (iii), but without (iv).

7. The method of claim 1, where achieving the predetermined alkane conversion percentage of 20% at a weight hourly space velocity of 100 h$^{-1}$ and a reaction temperature of 620° C. for the gallium-based alkane dehydrogenation catalyst occurs 27% to 31% sooner in air-soak treatment for the gallium-based alkane dehydrogenation catalyst undergoing the air-soak containing regeneration process using (i) through (iv) as compared to the gallium-based alkane dehydrogenation catalyst undergoing the air-soak containing regeneration process using (i) through (iii), but without (iv).

8. The method of claim 1, where achieving the predetermined alkane conversion percentage of 22% at a weight hourly space velocity of 100 h$^{-1}$ and a reaction temperature of 620° C. for the gallium-based alkane dehydrogenation catalyst occurs 22% to 26% sooner in air-soak treatment for the gallium-based alkane dehydrogenation catalyst undergoing the air-soak containing regeneration process using (i) through (iv) as compared to the gallium-based alkane dehydrogenation catalyst undergoing the air-soak containing regeneration process using (i) through (iii), but without (iv).

9. The method of claim 1, wherein the gallium-based alkane dehydrogenation catalyst includes a platinum (Pt) based promoter and an optional promotor metal on a catalyst support selected from the group consisting of aluminium oxide ($Al_2O_3$), silicon dioxide, silica-alumina composites, rare earth modified alumina, and combinations thereof.

10. The method of claim 9, where the optional promotor metal is potassium (K).

11. The method of claim 10, where the Pt based promoter provides a Pt loading of 0.1 to 500 parts per million (ppm) based on the total weight of the catalyst and the optional promoter has a K loading of 0 to 1 weight percent (wt. %) based on the total weight of the catalyst.

12. The method of claim 1, chlorine compound is selected from the group consisting of chlorinated hydrocarbons, HCl gas, chlorine ($Cl_2$) gas, and combinations thereof.

13. The method of claim 1, wherein the chlorine source is monochloroethane.

14. The method of claim 1, wherein the predetermined alkane conversion percentage is for propane.

15. An improved process for dehydrogenating an alkane, the process comprising placing an alkane in operative contact with a heated alkane dehydrogenation catalyst in a reactor, the catalyst comprising a Group VIII noble metal, a Group IIIA metal and, optionally, a promoter metal, removing from the reactor a partially deactivated catalyst, rejuvenating the partially deactivated catalyst in a regenerator, and transporting the rejuvenated catalyst from the regenerator to the reactor, wherein the improvement comprises a combination of treatment within the regenerator and transport of the rejuvenated catalyst from the regenerator to the reactor, the treatment within the regenerator comprising sequential steps:

a. heating the partially deactivated catalyst to a temperature of at least 660 degrees Celsius using heat generated combustion products obtained by combusting both coke contained on the partially deactivated catalyst and a fuel source other than the coke, the heating yielding a heated, further deactivated catalyst which has an alkane dehydrogenation activity that is less than that of the partially deactivated catalyst;

b. subjecting the heated, further deactivated catalyst to a conditioning step which comprises maintaining the heated, further deactivated dehydrogenation catalyst at a temperature of at least 660 degrees Celsius while exposing the heated, further deactivated dehydrogenation catalyst to a flow of an oxygen-containing gas with a chlorine or chlorine containing compound with an overall Cl concentration 0.1 ppm-volume to 100 ppm-volume for a period of time sufficient to yield an oxygen-containing reactivated dehydrogenation catalyst that has an activity for dehydrogenating alkane that is greater than that of either the partially deactivated catalyst or the further deactivated catalyst; and, optionally, c. maintaining the oxygen-containing reactivated catalyst at a temperature of at least 660 degrees Celsius while exposing the reactivated catalyst to a flow of stripping gas that is substantially free of molecular oxygen and combustible fuel for a period of time greater than two minutes and sufficient to remove from the oxygen-containing reactivated dehydrogenation catalyst at least a portion of molecular oxygen trapped within or between catalyst particles and chemisorbed oxygen that is desorbable at the temperature during that period of time and yield a rejuvenated dehydrogenation catalyst; with transport from the regenerator to the reactor being effected by a combination of gravity and motive force imparted by an inert transport gas.

16. A method of reducing a time of an air-soak treatment in a regeneration process, comprising:
   (i) removing surface carbon species from a gallium-based alkane dehydrogenation catalyst in a combustion process using a fuel gas; and
   (ii) conditioning, after the surface carbon species is removed from the gallium-based alkane dehydrogenation catalyst, the gallium-based alkane dehydrogenation catalyst in the air-soak treatment at a temperature of 660 degree Celsius (° C.) to 850° C. with (iii) a flow of oxygen-containing gas having (iv) 5 to 90 parts per million by volume (ppmv) of a chlorine source selected from chlorine, a chlorine compound or a combination thereof,
   wherein a predetermined alkane conversion percentage for the gallium-based alkane dehydrogenation catalyst undergoing the air-soak containing regeneration process is achieved using (i) through (iv) at least 10% to 50% sooner in air-soak treatment than a time required to achieve the same predetermined alkane conversion percentage for the gallium-based alkane dehydrogenation catalyst undergoing the air-soak treatment containing regeneration process using (i) through (iii), but without (iv).

* * * * *